US 6,550,689 B1

(12) United States Patent
Hoyes et al.

(10) Patent No.: US 6,550,689 B1
(45) Date of Patent: Apr. 22, 2003

(54) ANIMAL SCENT DISPENSING APPARATUS AND METHOD OF USE

(76) Inventors: David A. Hoyes, 235 Cameltown Hill Rd., Danville, PA (US) 17821; Brock A. Hoyes, 235 Cameltown Hill Rd., Danville, PA (US) 17821

( * ) Notice: Subject to any disclaimer, the term of this patent is extended or adjusted under 35 U.S.C. 154(b) by 0 days.

(21) Appl. No.: 09/517,992

(22) Filed: Mar. 3, 2000

Related U.S. Application Data

(60) Provisional application No. 60/122,735, filed on Mar. 4, 1999, and provisional application No. 60/129,856, filed on Apr. 17, 1999.

(51) Int. Cl.[7] ............................. B05B 17/00; A61L 9/04
(52) U.S. Cl. ........................ 239/1; 239/34; 239/44; 239/46; 239/47; 239/50; 239/57; 43/1; 119/711; 222/187
(58) Field of Search ....................... 239/34, 44, 45, 239/46, 47, 50, 57, 532, 600; 222/187, 321.7, 321.9, 174; 43/1; 119/711; 401/199, 207, 118

(56) References Cited

U.S. PATENT DOCUMENTS 3,856,209 A * 12/1974 Hickson ............... 239/532
4,682,715 A * 7/1987 Reeves ............... 239/145
4,867,076 A * 9/1989 Marcone ............... 109/20
5,148,949 A * 9/1992 Luca ............... 43/1
5,368,202 A * 11/1994 Smrt ............... 222/174
5,769,279 A * 6/1998 Smrt ............... 222/174

* cited by examiner

Primary Examiner—Lisa A. Douglas
(74) Attorney, Agent, or Firm—John J. Elnitski, Jr.

(57) ABSTRACT

An animal scent dispensing apparatus and method for dispensing animal scent. The animal scent dispensing apparatus provides for laying a scent trail, while a user is walking to a selected location in order to lure an animal. The animal scent dispensing apparatus provides the capability to refresh the scent trail while walking to the selected location. The animal scent dispensing apparatus includes a staff, a housing unit, a liquid absorbing dragging material and a container of animal scent. The housing unit is attached to the staff. The housing unit provides a chamber for the insertion of the container and for securing the dragging material. The container includes a spraying mechanism to release the scent from the container and onto the dragging material, when pressure is applied downward on the housing unit by the staff. Thereby, providing an easy method of making and refreshing a scent trail. The animal scent dispensing apparatus has particular utility for deer hunting wherein a scent can be dispensed at times and appropriateness, as determined by the user, when forming a scent trail for animals to follow.

30 Claims, 10 Drawing Sheets

ANIMAL SCENT DISPENSING APPARATUS AND METHOD OF USE

This application claims the benefit of U.S. Provisional Application Nos.: 60/122,735 filed Mar. 4, 1999 and 60/129,856 filed Apr. 17, 1999

BACKGROUND

Hunters attempt to lure animals, such as white tail deer, to a specific area by creating a scent trail which will pull the animals off their path of travel and toward the hunter. Animal scent is placed on an absorbent material referred to as a dragging material. The hunter drags the dragging material for a distance over/across animal paths and trails in order to make the scent trail. Animal scents, such as deer scent, are commonly used and commercially available in small bottles. Hunters apply a quantity of the scent product to the dragging material prior to dragging the dragging material on the ground. Hunters use many different absorbent materials of their own choice to make the dragging material. Such materials include cotton cord, felt strips, cotton balls dangling on the ground from a hand-held string, or strips of cotton T-shirts. Some hunters attach the dragging material directly to their boot or leg for dragging. Other hunters adapt the dragging material to be hand-held or attached to their waist, whereby it is allowed to extend to the ground with cord.

In all cases, the present method of applying scent to form a scent trail requires the user to continuously refresh the dragging material. The longer the scent trail made by the hunter, the more times the dragging material needs to be refreshed with more scent. The current methods require the hunter to stop, lift dragging material, find the bottle of scent in their pocket, and apply additional scent to the dragging material and then continue making the scent trail. The number of times the dragging material is refreshed with scent is dictated by hunting conditions. In some cases, it can be a considerable number of times based upon things such as dew or frost on the ground.

An object of the present invention is to provide a device for dispensing animal scent at a time and duration easily regulated by an individual when walking and making a scent trail.

Another object of the present invention is to provide a device for dispensing animal scent which has a reservoir so as to avoid having a hunter continuously opening a commercially available package of scent to re-apply scent, while making a scent trail.

Another object of the present invention is to provide a convenient method of laying a scent trail when a hunter is traveling to a final hunting destination.

Another object of the present invention is to provide an easy method to refresh the trail making material as required and dictated by the hunting conditions.

SUMMARY OF THE INVENTION

The present invention is an animal scent dispensing apparatus and method for dispensing animal scent. The animal scent dispensing apparatus includes a staff, a housing unit, a liquid absorbing dragging material and a container of animal scent. The housing unit is attached to the staff. The housing unit provides a chamber for the insertion of the container and for securing the dragging material. The container includes a spraying mechanism to release the scent from the container and onto the dragging material, when pressure is applied downward on the housing unit by the staff.

DETAILED DESCRIPTION OF THE INVENTION

The present invention is an animal scent dispensing apparatus 10 and method for dispensing animal scent. The animal scent dispensing apparatus 10 provides for laying a scent trail, while a user is walking to a selected location in order to lure an animal. The animal scent dispensing apparatus 10 provides the capability to refresh the scent trail while walking to the selected location. The animal scent dispensing apparatus 10 includes a staff 12, a housing unit 14, a liquid absorbing dragging material 16 and a container 18 of animal scent. The housing unit 14 is attached to the staff 12. The housing unit 14 provides a chamber 20 for the insertion of the container 18 and for securing the dragging material 16. The container 18 includes a spraying mechanism 22 to release the scent from the container 18 and onto the dragging material 16, when pressure is applied downward on the housing unit 14 by the staff 12. Thereby, providing an easy method of making and refreshing a scent trail. The animal scent dispensing apparatus 10 has particular utility for deer hunting wherein a scent can be dispensed at times and appropriateness, as determined by the user, when forming a scent trail for animals to follow.

Figure 1:
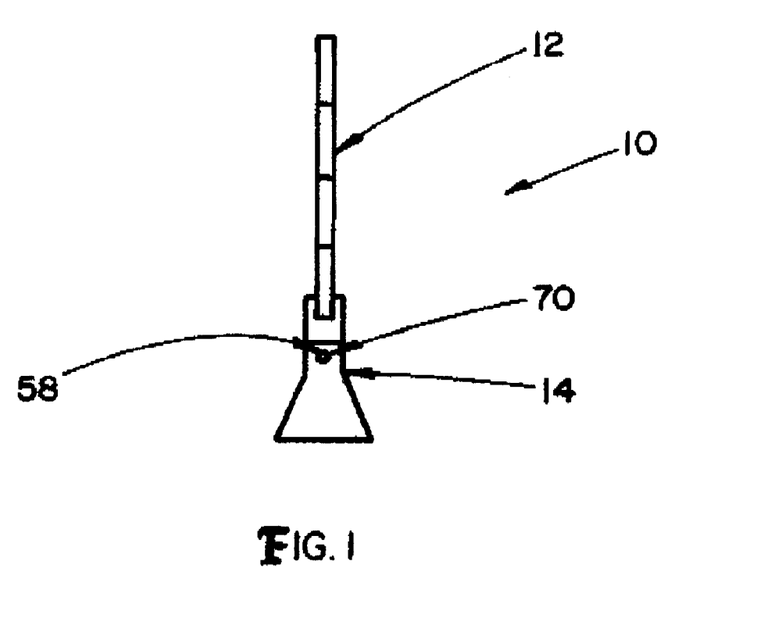
FIG. 1 is a perspective view of a animal scent dispensing apparatus according to the present invention.
Figure 2:
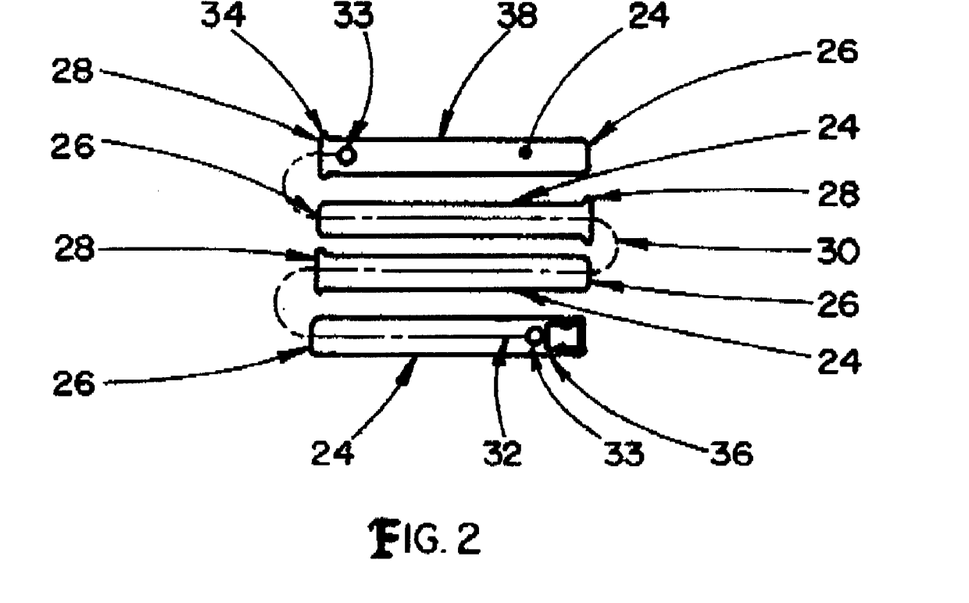
FIG. 2 is a perspective exploded view of a staff according to the present invention.

The staff 12 in FIGS. 1–2 is shown as a collapsible cane or walking stick, but the staff 12 could also be of a non-folding variety. The staff 12 as shown includes multiple tubular sections 24. Each tubular section 24 includes a male end 26 and female end 28. The male end 26 of one tubular section 24 fits into the female end 28 of another tubular section 24 to form the staff 12. The total length of the staff 12 being of the typical length of a cane or walking stick. The tubular sections 24 are held together by an elastic band 30. The elastic band 30 includes a first end 32 and a second end 34. The first end 32 of the elastic band 30 is secured to a top end 36 of the staff 12. The second end 34 of the elastic band 30 is secured to a bottom end 38 of the staff 12. Whereby, the elastic band 30 extends along the inside of all of the tubular sections 24. As an example, the first and second ends 32, 34 of the elastic band 30 can be connected to the staff ends 36, 38 by using a dowel 33 through the tubular sections 24 that are the top and bottom ends of the staff 12. The retractive force of the elastic band 30 holds the tubular sections 24 together, once the tubular sections 24 have been assembled as the staff 12. The staff 12 folds for the convenience of the user when not in use, by disassembling the tubular sections 24. The material the tubular sections 24 are made from can be plastic, wood, or metal, so long as the material provides enough strength and stability to withstand the pressure of an individual plunging or pushing the staff 12 against a surface.

Figure 3:
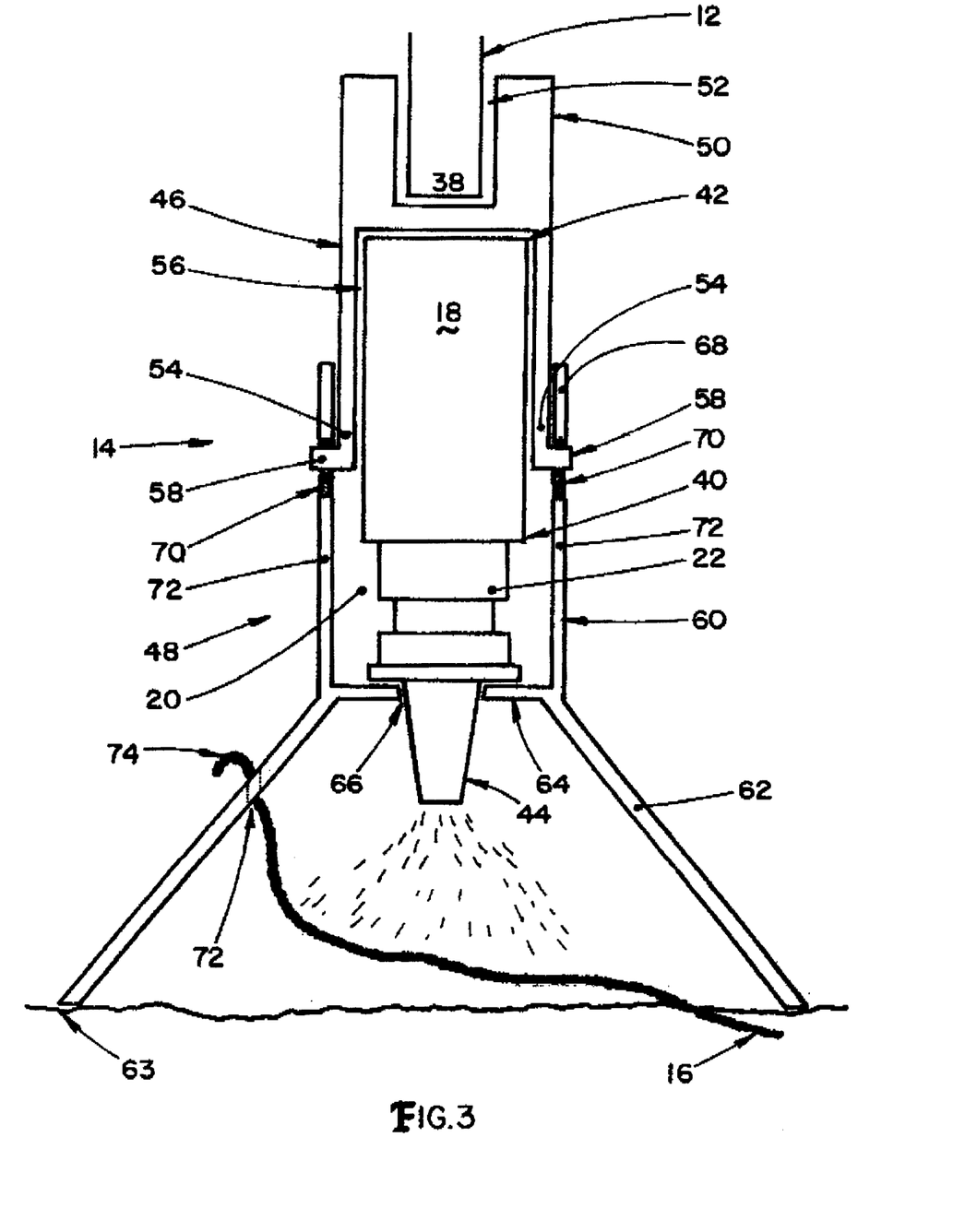
FIG. 3 is a front cross-sectional view of a housing unit according to the present invention.
Figure 4:
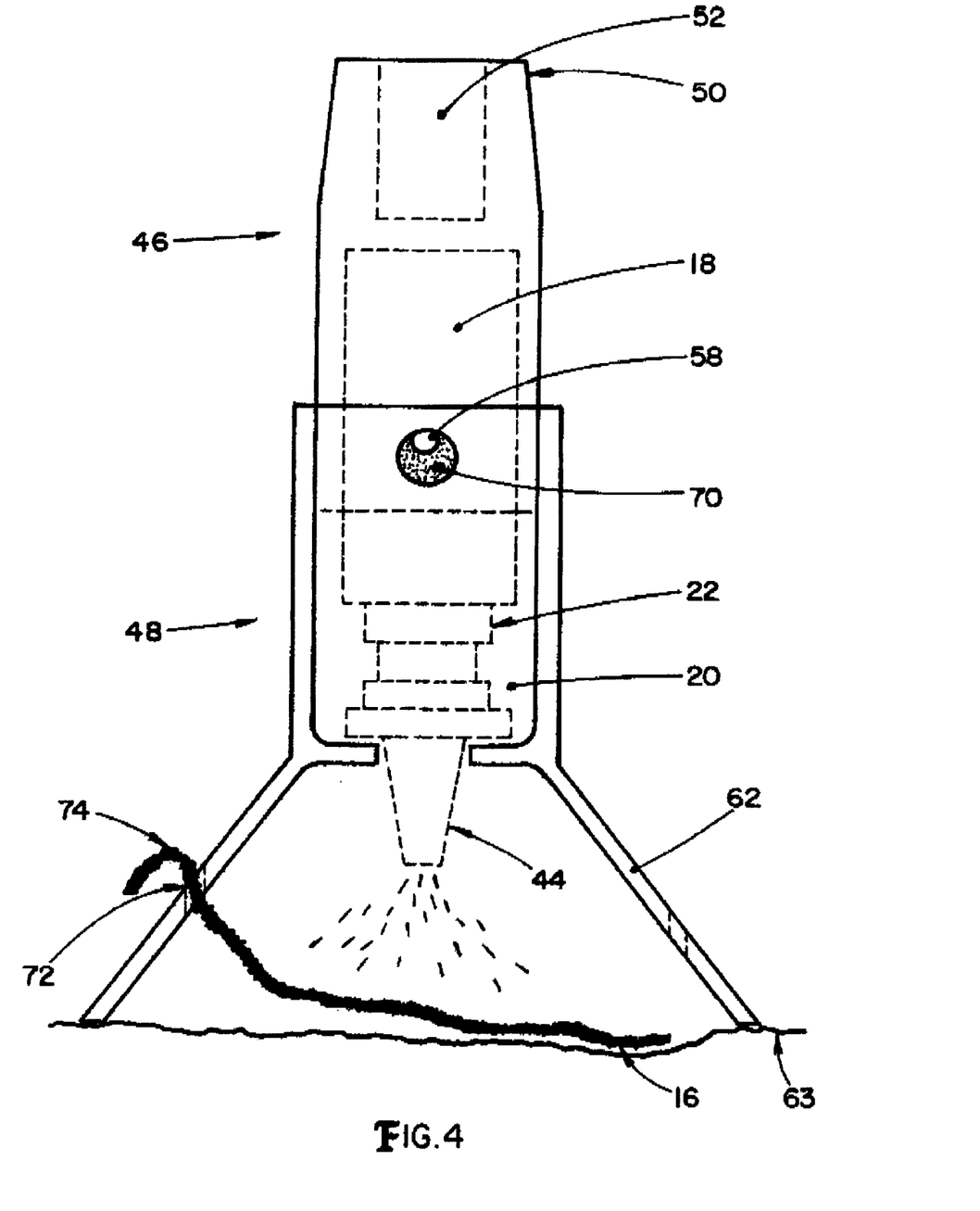
FIG. 4 is a side view of a housing unit according to the present invention.

The container 18 has a top 40 and a bottom 42, as shown in FIGS. 3–4. The top 40 of the container 18 is capped with the spraying mechanism 22. The spraying mechanism 22 is typical of a nasal sprayer, which is compressed to spray and automatically returns to an uncompressed position after activation. The spraying mechanism 22 includes a nozzle 44 to dispense the scent. An example of the container 18 is an industry standard plastic one ounce Boston round bottle fitted with an industry standard 20-410 threading to accept an industry standard 20-410 nasal sprayer.

The housing unit 14 is attached to the bottom end 38 of the staff 12. The housing unit 14 includes a male half 46 and a female half 48, as shown in FIGS. 3–4. The male half 46 is made of a flexible material and is cylindrical in shape. The top end 50 of male half 46 includes a staff socket 52 for insertion of the bottom end 38 of the staff 12. The staff 12 is held in place by the proper sizing of the staff socket 52 to be slightly smaller than the diameter of the bottom end 38 of the staff 12. As example, the bottom end 38 of the staff 12 having a diameter of three-quarter inches would require the staff socket 52 to be slightly smaller than three-quarter inches. A bottom end 54 of the male half 46 includes a container socket 56 for insertion of the bottom 42 of the container 18. Extending outward from sides of the bottom end 54 of the male half 46 are two stops 58.

The female half 48 of the housing unit 14 includes a cylindrical top section 60 and a funnel base 62. Between the top section 60 and the funnel base 62 is a support surface 64 to support the spraying mechanism 22 of the container 18. The support surface 64 includes a nozzle hole 66 to allow the nozzle 44 of the spraying mechanism 22 to be inserted, thereby providing for the nozzle 44 to be pointed toward the ground during use. A top end 68 of the top section 60 is opened ended and hollow to receive the bottom end 54 of the male half 46. Two round slots 70 are shown on the sides 72 of the top section 60 for receiving the stops 58 of the male half 46. The funnel base 62 extends from the top section 60 such that the wider part of the funnel base 62 extends away from the staff 12 and toward the ground 63. The funnel base 62 allows for the free standing of the animal scent dispensing apparatus 10 in a vertical position. The female half 48 is made from rigid material, such as hard plastic to provide stability to the housing unit 14, when the male and female halves 46, 48 are assembled. The funnel base 62 is sized to keep the nozzle 44 of the spraying mechanism 22 above the ground level during spraying and act as a wind barrier on windy days.

The housing unit 14 is formed by assembling the male and female halves 46, 48. Since the male half 46 is made from a flexible material, the male half 46 is squeezed at the bottom end 54 and inserted into the top end 68 of the top section 60 of the female half 48. The male half 46 is pushed into the female half 48 until the stops 58 pop into the round slots 70 and connect the male and female halves 46, 48 together. The stops 58 in the round slots 70 retain the male and female halves 46, 48 in an assembled position. The chamber 20 to hold the container 18 is formed by the container socket 46 of the male half 46 and the top section 60 of the female half 48. The container 18 is inserted between the male and female halves 46, 48 before assembly of the housing unit 14. Squeezing the two stops 58 back inside the top section 60 of the female half 48, while simultaneously pulling the male and female halves 46, 48 apart, disassembles the housing unit 14. The two stops 58 also allow the female half 48 to freely move up and down the male half 46, as the round slots 70 are larger than the stops 58. This up and down movement of the female half 48 is equal to at least the compression distance of the spraying mechanism 22 and allows the spraying mechanism 22 to function freely between its uncompressed and compressed positions.

Figure 5:
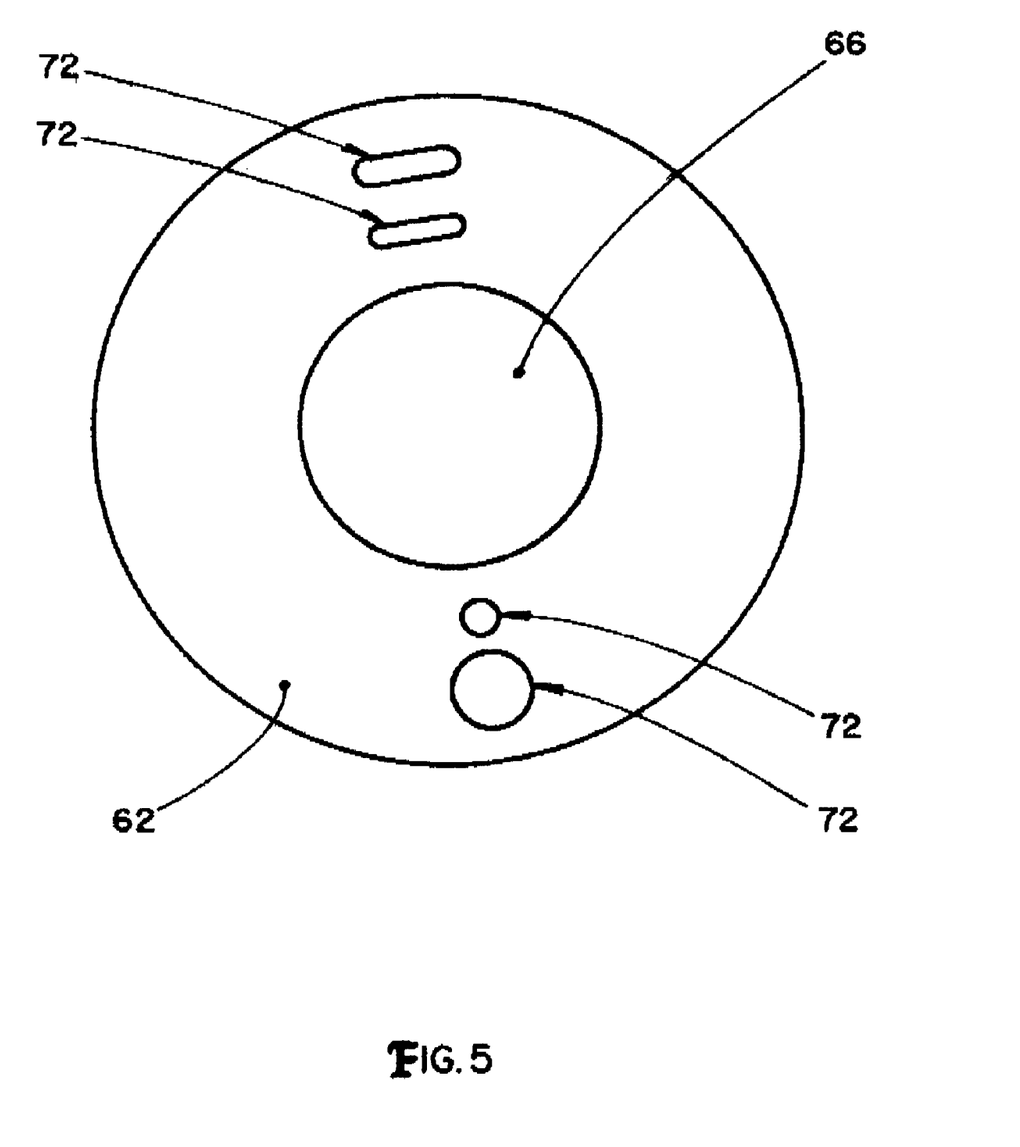
FIG. 5 is a bottom view of a base according to the present invention.

The housing unit 14 provides for the attachment of the dragging material 16, such as felt or cotton cord, that can be sprayed with the scent and dragged along the ground as the user walks. FIGS. 3–4 show the dragging material 16 attached to the funnel base 62 through an attachment hole 72. FIG. 5 shows a bottom view of the funnel base 62 displaying different types of attachment holes 72 to accommodate different sizes and types of dragging material 16. The dragging material 16 is attached by tying a knot 74 at the end of the dragging material 16, so it does not slip through the attachment hole 72. The length of the dragging material 16 is of a length that would continue to drag on the ground when the user is walking and lifting the staff during stride. When the user wants to refresh the dragging material 16, the user only has to rotate the staff 12 in either a clockwise or counterclockwise direction, which coils the dragging material 16 underneath the funnel base 62. The user would then push down on the staff 12, which compresses the spraying mechanism 22 of the container 18, due to the allowed motion between the male and female halves 46, 48. This motion activates the spraying of the scent from the nozzle 44 and onto the coiled dragging material 16 and the ground. The user then releases the downward force on the staff 12 which returns the spraying mechanism 22 to the uncompressed position and stops the release of scent.

Figure 6:
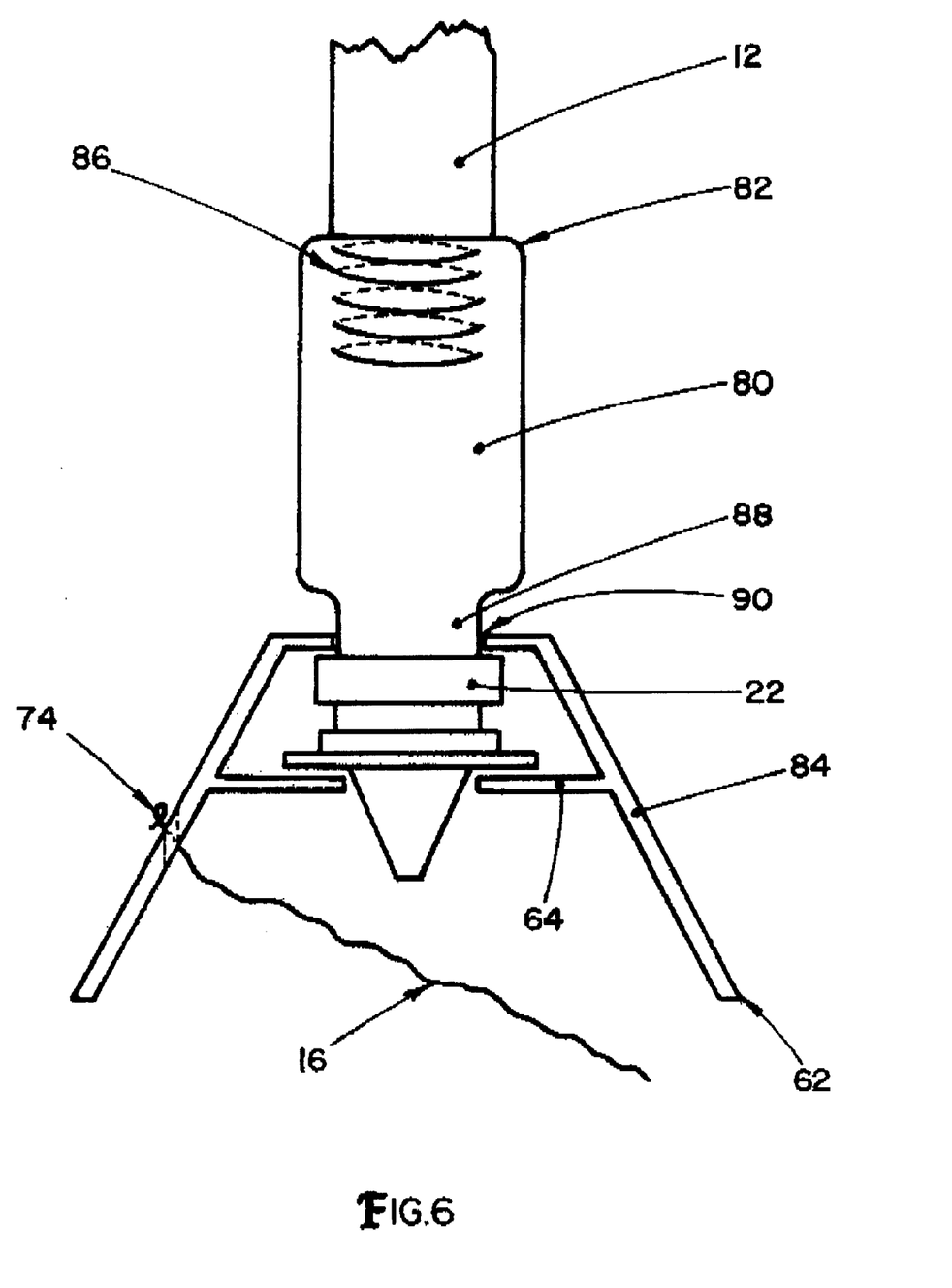
FIG. 6 is a perspective cutaway view of another embodiment of the animal scent dispensing apparatus according to the present invention.
Figure 7:
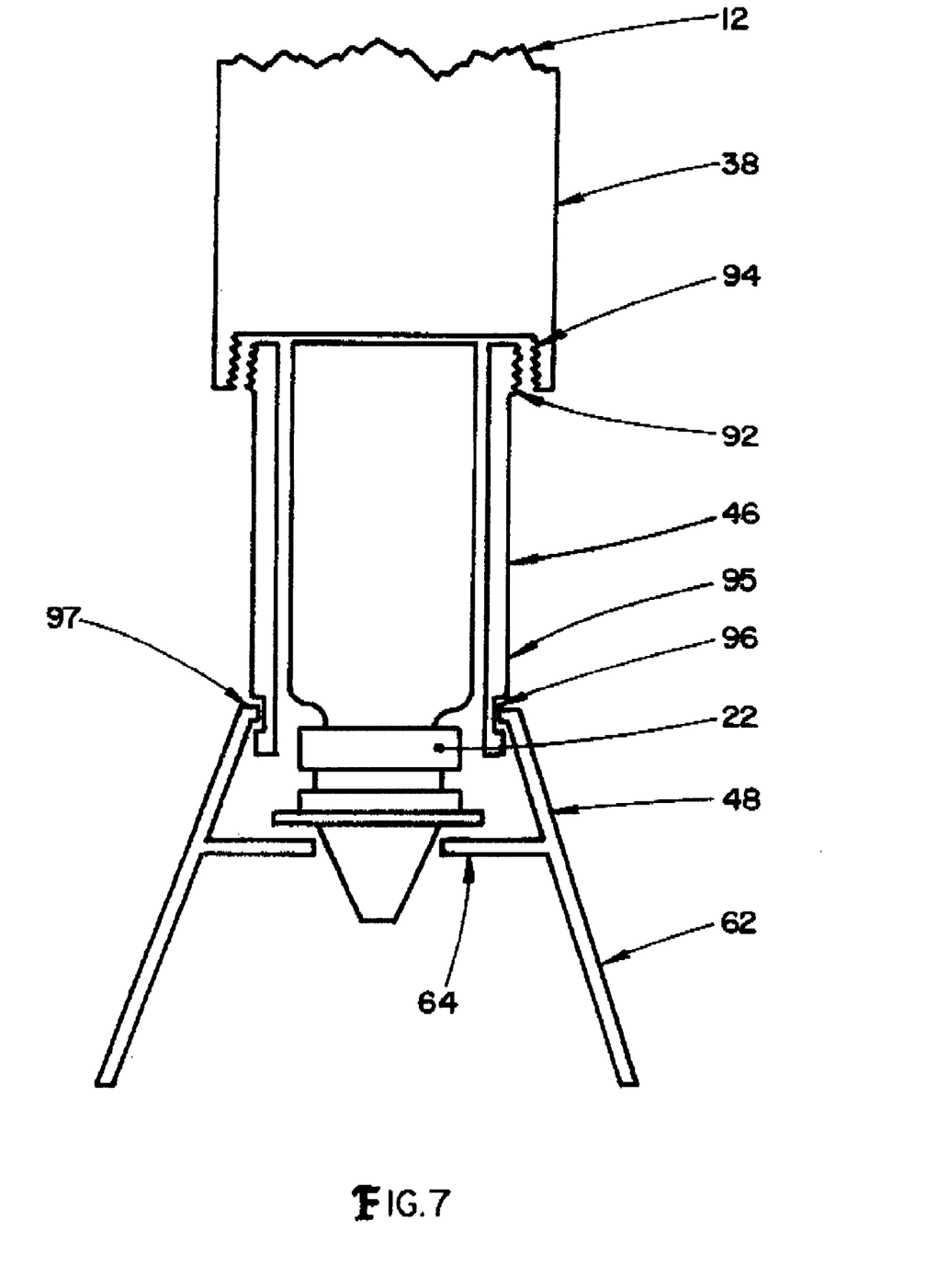
FIG. 7 is a perspective cutaway view of another embodiment of the animal scent dispensing apparatus according to the present invention.
Figure 8:
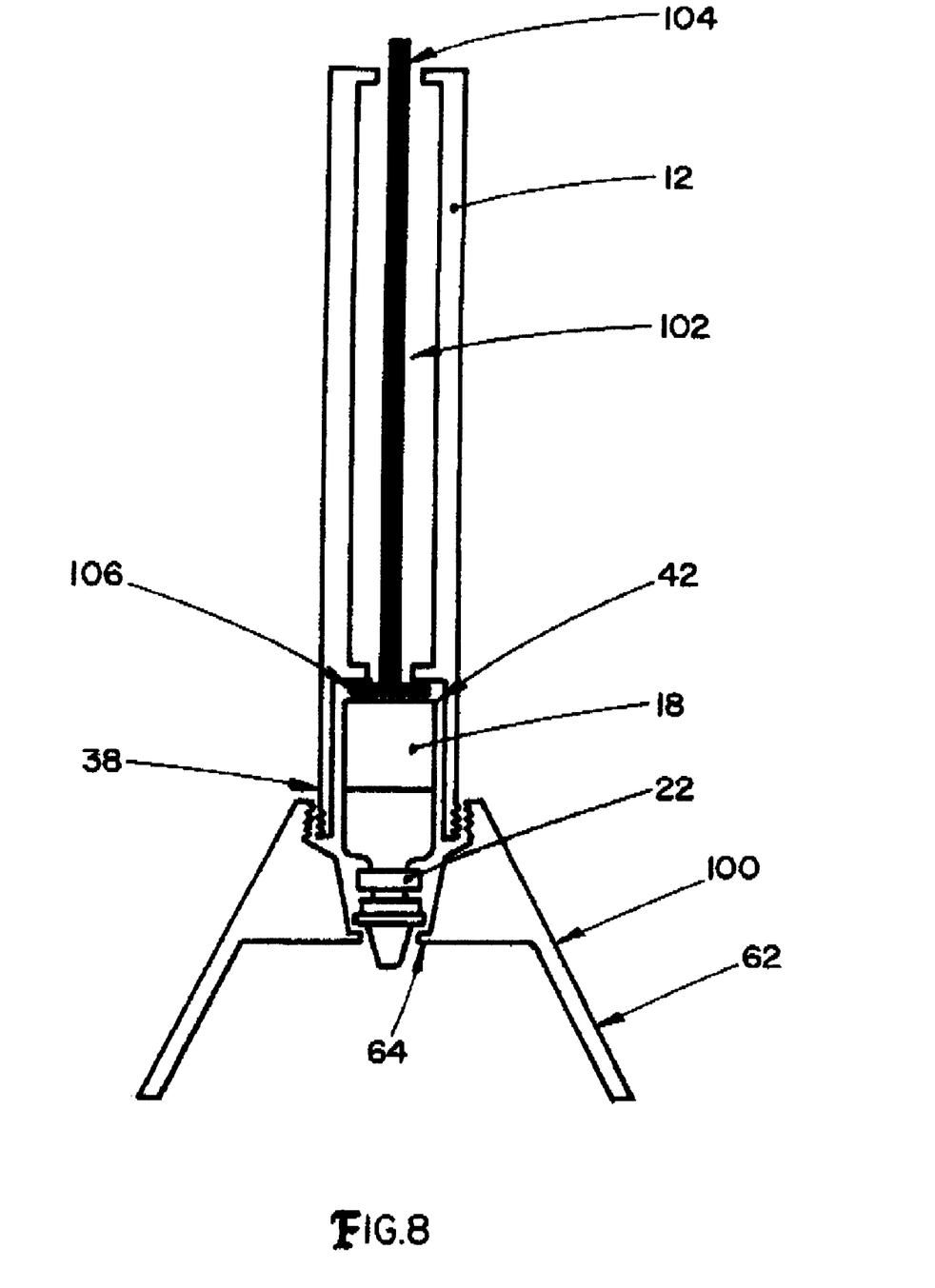
FIG. 8 is a cross-sectional view of another embodiment of the animal scent dispensing apparatus according to the present invention.
Figure 9:
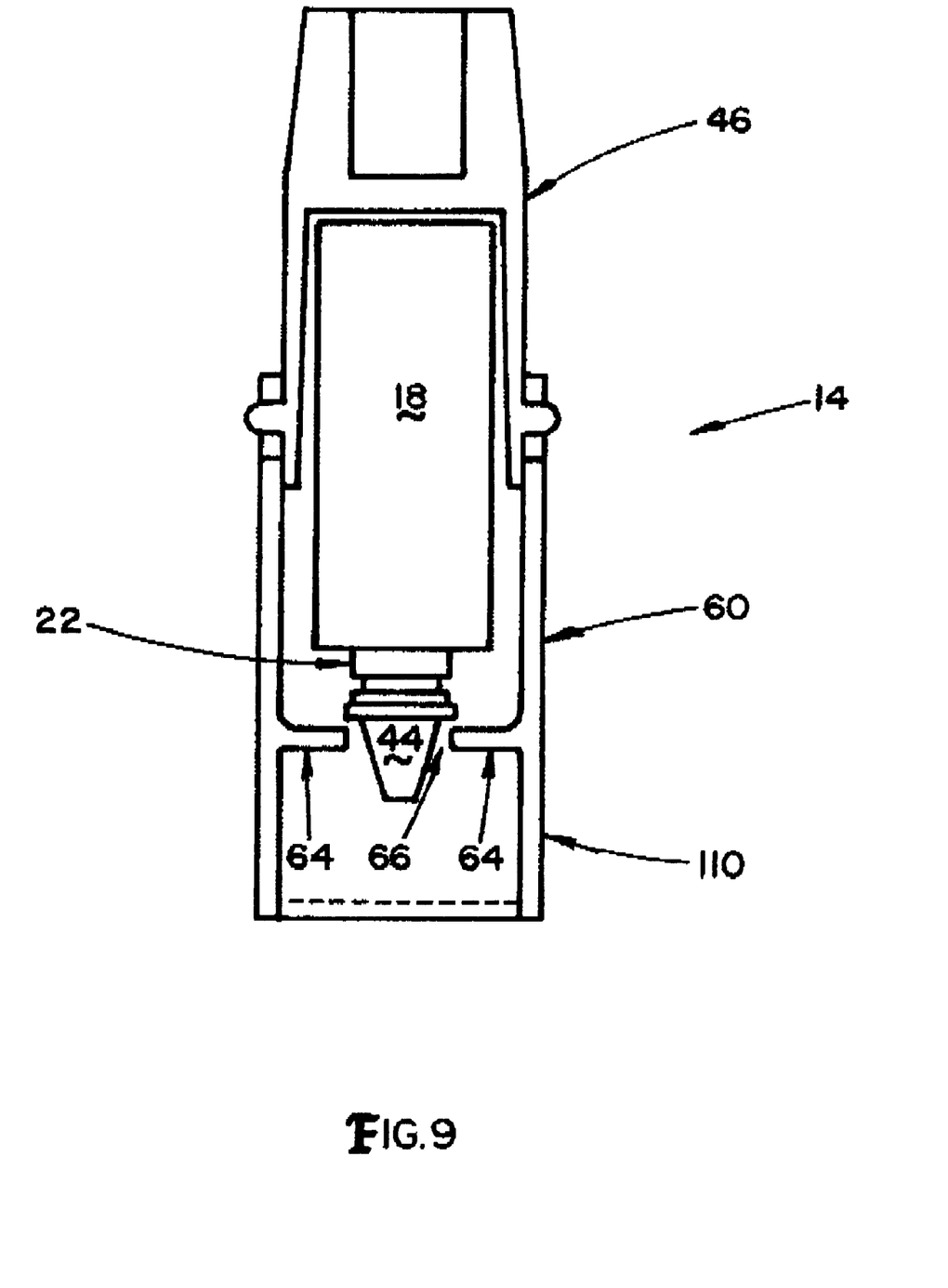
FIG. 9 is a cross-sectional view of another embodiment of the animal scent dispensing apparatus according to the present invention.
Figure 10:
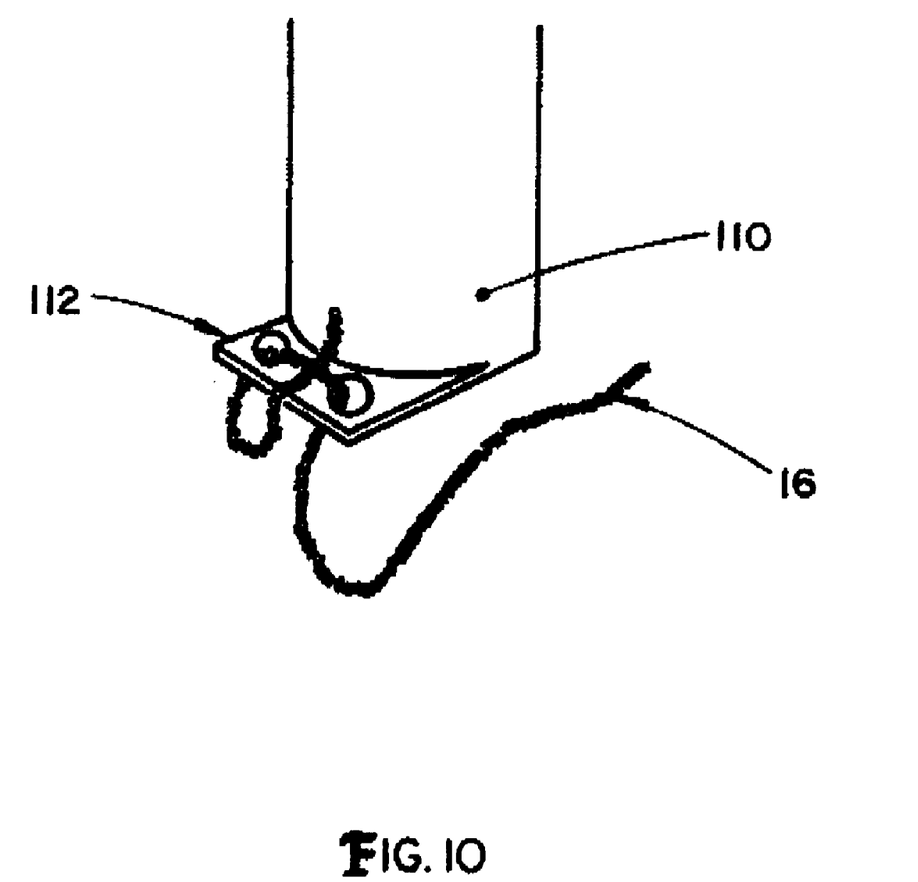
FIG. 10 is a perspective view of another embodiment of the animal scent dispensing apparatus according to the present invention.
Figure 11:
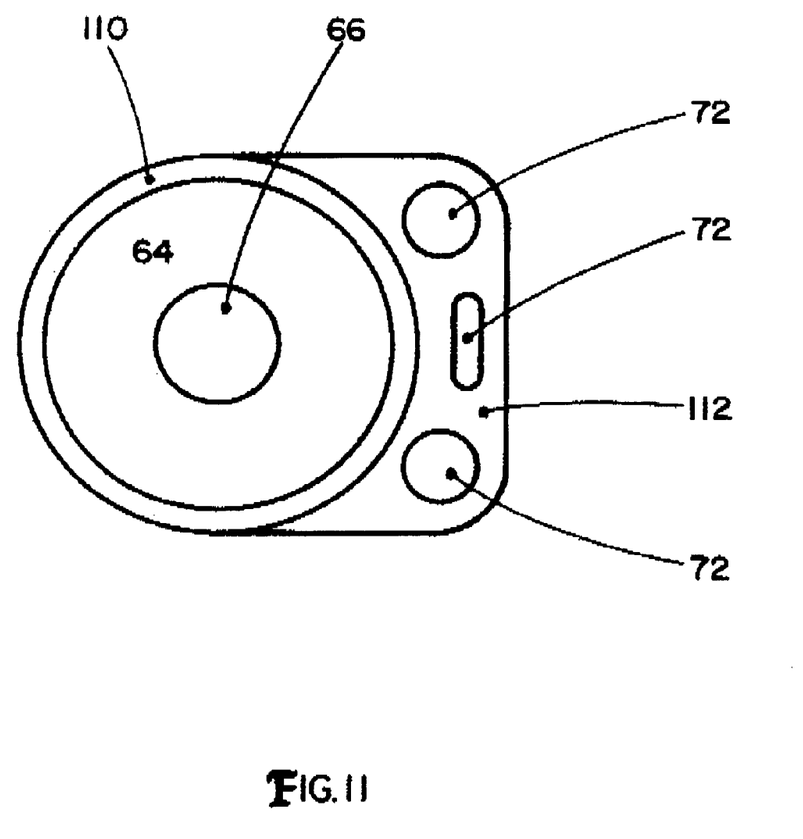
FIG. 11 is a bottom view of another embodiment of the animal scent dispensing apparatus according to the present invention.

FIGS. 6–11 show different envisioned embodiments of the animal scent dispensing apparatus 10 described above. FIG. 6 shows a container 80 with a specially molded bottom 82 and a one piece plunger housing 84. The bottom 82 includes an internal threading 86 inside the bottom 82 of the container 80 to receive a threaded end of the staff 12. The container 80 also has an extended neck 88. The plunger housing 84 includes the spraying mechanism 22 incorporated as part of the plunger housing 84. An end of the extended neck 88 is threaded (not shown). The extended neck 88 is inserted into a top 90 of the plunger housing 84, where the container 80 is threaded onto the spraying mechanism 22. The plunger housing 84 moves freely up and down the extended neck 88 of the container 80 to allow for the compression of the spraying mechanism 22. FIG. 7 shows a top end 92 of the male half 46 having an external threading on an outside of the top end 92 and the bottom end 38 of the staff 12 having an internal threaded socket 94 to receive the top end 92 of the male half 46. FIG. 7 also shows a modified male half 46 and female half 48 coupling. Shown in FIG. 7 is a bottom end 95 of the male half 46 having a slot 96 and a female half 48 having tabs 97 pointing inward. The tabs 97 fit into the slot 96 and are smaller than the slot 96. Whereby, the female half 48 slides up and down the male half 46 via the slot 96 and tabs 97 to activate the spraying mechanism 22. FIG. 8 shows a housing unit 100 in which the male and female halves 46, 48 and their movement are not necessary. Shown in FIG. 8 is a container 18 and spraying mechanism 22 in a one piece housing unit 100 having a funnel base 62. The staff 12 includes room at the bottom end 38 to receive the bottom 42 of the container 18. The staff 12 includes a rod 102 having a top end 104 and bottom end 106. The top end 104 of the rod 102 extends from the top end 108 of the staff 12. The bottom end 106 of the rod 102 extends against the bottom 42 of the container 18. When the top end 104 of the rod 102 is depressed by the user, the bottom end 106 of the rod 102 pushes against the bottom 42 of the container 18 and activates the spraying mechanism 22. Thereby, eliminating the need to push the housing unit 100 against the ground to activate the spraying mechanism 22. FIGS. 9–11 show a different shaped base and method of securing the dragging material 16 to the base. FIGS. 8–10 show a cylindrical base 110 that replaces the funnel base 62. FIGS. 10–11 show a mounting tab 112 on an outside surface of the cylindrical base 110. The mounting tab 112 includes attachment holes 72 to attach the dragging material 16. Also envisioned is the use of a telescoping staff (not shown) instead of a foldable staff and different shapes (not shown) for the round slots 70.

While embodiments of the invention have been described in detail herein, it will be appreciated by those skilled in the art that various modifications and alternatives to the embodiments could be developed in light of the overall teachings of the disclosure. Accordingly, the particular arrangements are illustrative only and are not limiting as to the scope of the invention which is to be given the full breadth of any and all equivalents thereof.

We claim:

1. An animal scent dispensing apparatus comprising:
   a staff having a top and a bottom, said top to be held by a user and said bottom to be held toward terrain traveled by the user;
   a container;
   a spraying mechanism connected to said container; and
   a housing unit directly attached to said bottom of said staff, said housing for holding said container and spraying mechanism, said housing adapted to allow the user to spray contents of said container onto the terrain when said staff is a mostly vertical orientation, and said housing unit activates said spraying mechanism when said housing unit is pushed against a surface by said staff.

2. The animal scent dispensing apparatus of claim 1, further including a dragging material attached to said housing unit which absorbs liquid.

3. The animal scent dispensing apparatus of claim 1, wherein said staff is foldable.

4. The animal scent dispensing apparatus of claim 3, wherein said staff comprises a series of tubular sections that can be assembled and disassembled.

5. The animal scent dispensing apparatus of claim 3, wherein said staff is telescopic.

6. The animal scent dispensing apparatus of claim 1, wherein said spraying mechanism includes a nozzle, a compressible top and a bottom; wherein said nozzle extends from said compressible top, said bottom connects to said container and said compressible top attaches and is compressible against said bottom in order to release contents of said container; and wherein said spraying mechanism is similar to a nasal sprayer having a compressed and uncompressed positions.

7. An animal scent dispensing apparatus comprising:
   a staff having a top and a bottom, said top to be held by a user and said bottom to be held toward terrain traveled by the user;
   a container;
   a spraying mechanism connected to said container; and
   a housing unit directly attached to said bottom of said staff, said housing for holding said container and spraying mechanism and said housing adapted to allow the user to spray contents of said container onto the terrain when said staff is a mostly vertical orientation
   a rod in said staff which pushes against said container when pushed by a user and activates said spraying mechanism in said housing unit.

8. The animal scent dispensing apparatus of claim 1, further including a rod in said staff which pushes against said container when pushed by a user and activates said spraying mechanism in said housing unit.

9. The animal scent dispensing apparatus of claim 1, wherein said housing unit comprises a male half and a female half, wherein said male and female halves form a chamber to hold said container, and wherein movement is allowed between said male and female halves to activate said spraying mechanism.

10. The animal scent dispensing apparatus of claim 9, wherein said female half includes a base having a top and a bottom, a support surface near said top of said base to support said spraying mechanism above said bottom of said base and a hole in said support surface to allow a portion of said spraying mechanism to extend into the said base.

11. The animal scent dispensing apparatus of claim 10, wherein said portion of said spraying mechanism is a nozzle.

12. The animal scent dispensing apparatus of claim 9, wherein said male half includes a bottom end and said female half includes a top section, wherein said bottom end of said male half includes at least one stop and said top section of said female half includes at least one slot to receive and allow movement of said stop.

13. The animal scent dispensing apparatus of claim 9, wherein a part of said housing unit is a funnel shaped base.

14. The animal scent dispensing apparatus of claim 9, wherein said male half includes a staff socket to receive said staff.

15. The animal scent dispensing apparatus of claim 9, wherein said male half includes external threading and said staff includes internal threading on a bottom end of said staff in order to mate said staff and said male half.

16. The animal scent dispensing apparatus of claim 1, wherein said container includes a bottom having internal threading to receive said staff having a threaded end.

17. The animal scent dispensing apparatus of claim 1, wherein a bottom of said container is attached to said staff; wherein said housing unit includes said spraying mechanism as part of said housing unit and said container is inserted into said housing unit to attach said container to said spraying mechanism; wherein said housing unit can move along a neck of said container to activate said spraying mechanism.

18. A method of making a scent trail comprising, pushing downward on a staff connected to a container to activate a spraying mechanism and spray scent from the container, wherein the staff includes a top and a bottom, the top to be held by a user and the bottom to be held toward terrain traveled by the user, wherein a housing unit is directly attached to the bottom of the staff, the housing for holding a container and spraying mechanism attached to the container and wherein the housing is adapted to allow the user to spray contents of the container onto terrain to make the scent trail when the staff is a mostly vertical orientation.

19. The method of claim 18, further including a dragging material attached below the spraying mechanism; further spraying said dragging material with the spraying mechanism; and dragging said dragging material along a trail.

20. An animal scent dispensing apparatus, for use with a staff provided by a user, comprising:

a container;

a spraying mechanism connected to said container; and a housing unit adapted to receive a bottom of the staff provided by the user, said housing for holding said container and spraying mechanism, said housing adapted to allow the user to attach the staff provided by the user and spray contents of said container onto the terrain when the staff provided by the user is in a mostly vertical orientation, and said housing unit activates said spraying mechanism when said housing unit is pushed against a surface by the staff provided by the user.

21. The animal scent dispensing apparatus of claim 20, wherein said spraying mechanism includes a nozzle, a compressible top and a bottom; wherein said nozzle extends from said compressible top, said bottom connects to said container and said compressible top attaches and is compressible against said bottom in order to release contents of said container; and wherein said spraying mechanism is similar to a nasal sprayer having a compressed and uncompressed positions.

22. The animal scent dispensing apparatus of claim 20, wherein said housing unit comprises a male half and a female half, wherein said male and female halves form a chamber to hold said container, and wherein movement is allowed between said male and female halves to activate said spraying mechanism.

23. The animal scent dispensing apparatus of claim 22, wherein said female half includes a base having a top and a bottom, a support surface near said top of said base to support said spraying mechanism above said bottom of said base and a hole in said support surface to allow a portion of said spraying mechanism to extend into the said base.

24. The animal scent dispensing apparatus of claim 23, wherein said portion of said spraying mechanism is a nozzle.

25. The animal scent dispensing apparatus of claim 22, wherein said male half includes a bottom end and said female half includes a top section, wherein said bottom end of said male half includes at least one stop and said top section of said female half includes at least one slot to receive and allow movement of said stop.

26. The animal scent dispensing apparatus of claim 22, wherein a part of said housing unit is a funnel shaped base.

27. The animal scent dispensing apparatus of claim 22, wherein said male half includes a staff socket to receive said staff.

28. The animal scent dispensing apparatus of claim 22, wherein said male half includes external threading and said staff includes internal threading on a bottom end of said staff in order to mate said staff and said male half.

29. The animal scent dispensing apparatus of claim 20, wherein said container includes a bottom having internal threading to receive said staff having a threaded end.

30. The animal scent dispensing apparatus of claim 20, wherein a bottom of said container is attached to said staff; wherein said housing unit includes said spraying mechanism as part of said housing unit and said container is inserted into said housing unit to attach said container to said spraying mechanism; wherein said housing unit can move along a neck of said container to activate said spraying mechanism.

* * * * *